United States Patent [19]

Suami

[11] 4,039,578
[45] Aug. 2, 1977

[54] 1-TETRAHYDROXYCYCLOPENTYL-3-NITROSO-3-(2-CHLOROETHYL)-UREA ANTITUMOR AGENTS

[76] Inventor: Tetsuo Suami, 3-5-8, Nakamachi, Musashino, Tokyo 180, Japan

[21] Appl. No.: 664,844

[22] Filed: Mar. 8, 1976

[51] Int. Cl.$^2$ .................. C07C 127/15; C07C 133/06; A61K 31/17; A61K 31/175

[52] U.S. Cl. ................................ 260/553 R; 424/322; 424/323; 260/554

[58] Field of Search ............................ 260/553 R, 554

[56] References Cited

U.S. PATENT DOCUMENTS 3,859,277  1/1975  Murakami et al. .......... 260/553 R X

OTHER PUBLICATIONS

Wheeler et al., Cancer Research, 34, 194–200, Jan. 1974.
Johnston et al., J. Med. Chem. 9:892–911 (1966) and J. Med. Chem. 14 : 600–614 (1971).
Serrou et al., C. R. Hebd. Seances Acad. Sci., Ser. D 1974, 279(8), 703–706.
Montero et al., C. R. Hebd. Seances Acad. Sci., Ser. C 1974, 279(18), 809–811.
Anderson et al., Cancer Research, 35:761–765 (1975).
Johnston et al., J. Med. Chem. 18(1):104–106 (1975).
Suami et al., Bull. Chem. Soc. Japan, 46:2562–2564 (1973).

*Primary Examiner*—Daniel E. Wyman
*Assistant Examiner*—Thomas A. Waltz
*Attorney, Agent, or Firm*—David M. Morse

[57] ABSTRACT

Novel water-soluble nitrosourea derivatives of the formula

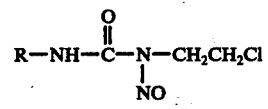

wherein R represents a 2′, 3′, 4′, 5′-tetrahydroxycyclopentyl group exhibit high effectiveness in various animal tumor systems.

12 Claims, No Drawings

1-TETRAHYDROXYCYCLOPENTYL-3-NITROSO-3-(2-CHLOROETHYL)-UREA ANTITUMOR AGENTS

BACKGROUND OF THE INVENTION

1. Field of the Invention

This invention relates to novel nitrosourea derivatives useful in treating various rodent tumor systems.

2. Description of the Prior Art

Cancer is now the second leading cause of death in the United States and it is believed that the proportion of deaths due to cancer will climb in coming years throughout the world due to such factors as the increase in the average life span, the large number of persons completing 20–30 years as active smokers, environmental carcinogens and the more widespread use of various preservatives in foods and other substances which are injested. The trend in cancer therapy is now in the direction of earlier and more universal use of chemotherapy alone or in conjunction with radiation and surgery, in contrast to previous use of chemotherapy as a last resort in surgically inoperative cases.

Various nitrosourea compounds have been disclosed in the literature as active therapeutic agents for the treatment of experimental and clinical neoplasms. The three members of this class which have been clinically studied are BCNU [1,3-bis(2-chloroethyl)-1-nitrosourea], CCNU [1-(2-chloroethyl)-3-cyclohexyl-1-nitrosourea] and methyl CCNU [1-(2-chloroethyl)-3-(4-methylcyclohexyl)-1-nitrosourea]. These compounds have been shown to have activity either alone or in combination with other agents against primary brain tumors, malignant melanoma, lymphomas and a few selected solid tumors.

Johnson and his co-workers disclose BCNU, CCNU and methyl CCNU and a large number of nitrosourea analogs of these three compounds (including compounds of the formula

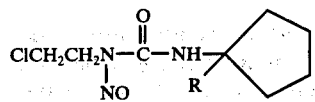

where R is hydrogen or methyl) in J. Med. Chem. 14:600-614 (1971) and J. Med. Chem. 9:892-911 (1966).

Recently, attempts have been made to prepare nitrosoureas of several amino sugars including D-glucosamine, 1-amino-1-deoxy-2,3-O-isopropylidene-D-ribofuranose and 1-amino-1-deoxy-D-ribopyranose [see, for example, J. Med. Chem. 18(1):104-106 (1975) and C. R. Hebd. Seances Acad. Sci., Series D, 279(8):703-706 and 279(18):809-811(1974)]. Schein, et al., reports in Cancer Research 35:761-765 (1975) that chlorozotocin, the 2-chloroethyl analog of the anticancer antibiotic streptozotocin, has antitumor activity against the L-1210 mouse leukemia system but appears to have greatly reduced bone marrow toxicity relative to the three above-mentioned nitrosourea antitumor agents in clinical use. Chlorozotocin has the chemical name 2-[3-(2-chloroethyl)-3-nitrosoureido]-2-deoxy-D-glucopyranose and the structure

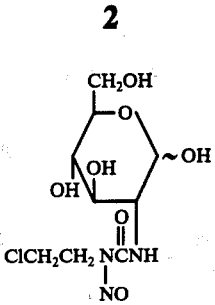

Suami in Bull. Chem. Soc. Japan 46:2562-2564 (1973) suggests that the cyclopentane ring is both hydrolytically and enzymatically more stable than a ribofuranosyl moiety and discloses several cyclopentanetetrol analogs of purine nucleosides.

SUMMARY OF THE INVENTION

The present invention provides novel water-soluble antitumor agents having the formula

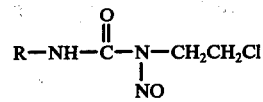

I wherein R represents a 2',3',4',5'-tetrahydroxycyclopentyl group. The compounds of formula I inhibit the growth of various tumor systems in mice such as L-1210 lymphatic leukemia, P-388 lymphatic leukemia and Lewis Lung Carcinosarcoma.

The compounds of the present invention may be prepared by the process comprising the consecutive steps of 1. condensing a 5-amino-1,2,3,4-cyclopentanetetrol with 2-chloroethyl isocyanate in an inert solvent system at a temperature of from about −20° C. to 100° C. to form a ureido intermediate of the formula

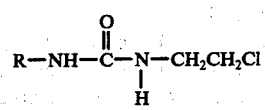

II wherein R represents a 2',3',4',5'-tetrahydroxycyclopentyl group; and 2. subjecting intermediate II to nitrosation in an aqueous solvent system at a temperature of from about −20° C. to 50° C. to form the desired compound of formula I.

The 5-amino-1,2,3,4-cyclopentanetetrol starting materials or the pentaacetyl derivatives thereof are disclosed by Suami, et al. in J. Org. Chem. 38(21):3691-3696 (1973). The ten possible stereoisomers are shown below together with the nomenclature used for the different isomeric forms. The position and configuration of the hydroxyl substituents is indicated by the lines above and below the plane of the cyclopentyl ring system.

a) 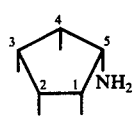

1,2,3,4,5/0-5-amino-1,2,3,4-cyclopentanetetrol b) 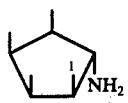

1,2,3,4/5-5-amino-1,2,3,4-cyclopentanetetrol

-continued c) 

1,4,5/2,3-5-amino-1,2,
3,4-cyclopentanetetrol d) 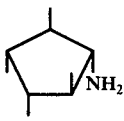

1,4/2,3,5-5-amino-1,2,
3,4-cyclopentanetetrol e) 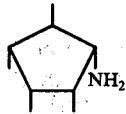

1,2,3,5/4-5-amino-1,2,
3,4-cyclopentanetetrol f) 

1,2,4,5/3-5-amino-1,2,
3,4-cyclopentanetetrol g) 

1,2,3/4,5-5-amino-1,2,
3,4-cyclopentanetetrol h) 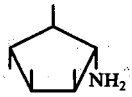

1,2,4/3,5-5-amino-1,2,
3,4-cyclopentanetetrol i) 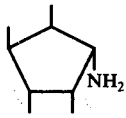

1,2,5/3,4-5-amino-1,2,
3,4-cyclopentanetetrol j) 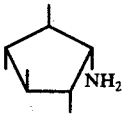

1,3,5/2,4-5-amino-1,2,
3,4-cyclopentanetetrol

Isomers a–d above are meso forms while e–j are racemic diastereomers of which only one enantiomer has been shown. The present invention includes within its scope compounds of formula I prepared from the meso starting materials of formulae a–d, the racemic isomers of formulae e–j and the resolved epimers of isomers e–j.

The 5-amino-1,2,3,4-cyclopentanetetrol starting materials may be obtained from the corresponding pentaacetyl derivatives disclosed by Suami by deacetylation with hydrochloric acid.

The condensation step (1) in the above reaction is carried out in an inert solvent system. Examples of suitable inert solvents are water, (lower)alkanols such as methanol, ethanol, propanol or butanol, water-(lower-)alkanol mixtures such as aqueous methanol, aqueous ethanol, etc., and inert organic solvents such as dioxane. The preferred solvent systems are those comprising either water or aqueous (lower)-alkanols, e.g. 50% aqueous ethanol. The condensation reaction may be conducted over a wide range of temperatures, i.e. from about −20° to 100° C., but is preferably performed at a temperature of around 0° C. and with stirring.

Nitrosation step (2) is carried out according to conventional procedures. Thus, the ureido intermediate II may be reacted in an aqueous solvent system with nitrous acid or a source thereof, e.g. by in situ generation from a nitrite compound such as sodium nitrite, potassium nitrite or amyl nitrite or dinitrogen trioxide and an aqueous organic or mineral acid such as formic acid, acetic acid, propionic acid or hydrochloric acid. The temperature for the nitrosation reaction may range from about −20° C. to 50° C. and is most preferably about 0° C.

A preferred embodiment of the present invention is the isomer having the chemical name (1,4/2,3,5)-5-[3-(2-chloroethyl)-3-nitrosoureido]-1,2,3,4-cyclopentanetetrol and the structure

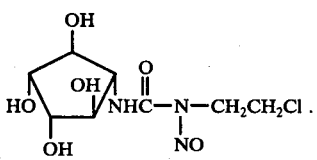

TE-5

Another preferred embodiment of the present invention is the isomer having the chemical name (1,2,3,4/5)-5-[3-(2-chloroethyl)-3-nitrosoureido]-1,2,3,4-cyclopentanetetrol and the structure

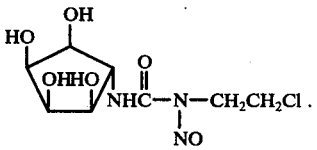

TE-6

Still another preferred embodiment of the present invention is the racemic compound having the chemical name DL-(1,2,4/3,5)-5-[3-(2-chloroethyl)-3-nitrosoureido]-1,2,3,4-cyclopentanetetrol and the structure

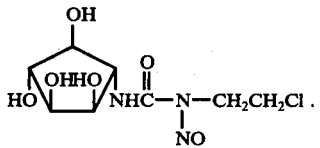

TE-7

The compounds of the present invention were tested against several transplantable mouse tumors and the results of these tests are shown below in Tables 1 through 6. The methodology used generally followed the protocols of the National Cancer Institute for Lymphatic Leukemias P-388 and L-1210 and for Lewis Lung Carcinoma [see, for example, Cancer Chemotherapy Rep. 50:79–84 (1966) and Cancer Chemotherapy Rep. Part 3. 3:1–103 (1972)]. The essential experimental details are given at the bottom of each of the tables.

TABLE 1

| Effect of compound TE-5 on P-388 Mouse Leukemia | | | | |
|---|---|---|---|---|
| Compound | Dose mg/kg/day | MST Days | Effect MST %T/C | Average Weight Change in g. | Survivors Day 5 |
| TE-5 | 32 | 14.0 | 133 | +0.1 | 6/6 |
| TE-5 | 16 | 21.0 | 200 | +0.6 | 6/6 |
| Control | Saline | 10.5 | — | +1.4 | 10/10 |

Tumor inoculum: $10^6$ ascitic cells implanted i.p.
Host: CDF$_1$ ♂ with P-388.
Treatment: Once daily for 9 days starting Day 1.
Evaluation: MST = Median survival time in days.
Effect: % T/C = MST treated/MST control × 100.
Criteria: T/C≧125 considered significant tumor inhibition (prolongation of host survival).

TABLE 1-continued

Effect of compound TE-5 on P-388 Mouse Leukemia

| Compound | Dose mg/kg/day | MST Days | Effect MST %T/C | Average Weight Change in g. | Survivors Day 5 |
|---|---|---|---|---|---|

Survivors: Day 5 Toxicity evaluation, weight change recorded.
TE-5 = Compound of Example 1.

TABLE 2

Effect of TE-5 and Standard Agents on Lewis Lung Carcinoma

| Compound | Dose Days Treated | Schedule Total Injections | Dose mg/kg/inj | MST Days | Effect MST %T/C | Average Weight Change in g. | Survivors Day 5 | Survivors Day 60 |
|---|---|---|---|---|---|---|---|---|
| Me CCNU | 7,12 | 2 | 24 | 33.5 | 168 | +0.7 | 6/6 | 0/6 |
| Me CCNU | 7,12 | 2 | 16 | 30.0 | 150 | −0.2 | 6/6 | 1/6 |
| CCNU | 7,15 | 2 | 50 | 25.5 | 128 | +0.3 | 6/6 | 0/6 |
| CCNU | 7,15 | 2 | 33 | 24.0 | 120 | +0.8 | 6/6 | 0/6 |
| BCNU | 7,13 | 2 | 39 | 17.0 | 85 | +0.6 | 6/6 | 0/6 |
| BCNU | 7,13 | 2 | 26 | 21.0 | 105 | +0.5 | 6/6 | 0/6 |
| CTX | 7,14,21,28 | 4 | 150 | 22.0 | 110 | +0.3 | 6/6 | 0/6 |
| TE5 | 7,14 | 2 | 256 | 12.0 | 60 | +0.4 | 6/6 | 0/6 |
| TE5 | 7,14 | 2 | 128 | 12.0 | 60 | +0.7 | 6/6 | 0/6 |
| TE5 | 7,14 | 2 | 64 | 13.5 | 68 | +1.1 | 0/6 | 0/6 |
| TE5 | 7,14 | 2 | 32 | 29.0 | 145 | −1.3 | 6/6 | 1/6 |
| TE5 | 7,14 | 2 | 16 | 23.0 | 115 | +0.9 | 4/5 | 1/5 |
| TE5 | 7,14 | 2 | 8 | 20.0 | 100 | −1.0 | 6/6 | 0/6 |
| TE5 | 1→11 | 11 | 128 | Tox | — | — | 0/6 | 0/6 |
| TE5 | 1→11 | 11 | 64 | Tox | — | — | 0/6 | 0/6 |
| TE5 | 1→11 | 11 | 32 | 6.5 | 33 | −2.7 | 6/6 | 0/6 |
| TE5 | 1→11 | 11 | 10 | 12.0 | 60 | −2.4 | 6/6 | 0/6 |
| TE5 | 1→11 | 11 | 8 | 28.5 | 143 | −0.9 | 6/6 | 0/6 |
| TE5 | 1→11 | 11 | 4 | 32.5 | 163 | −0.3 | 6/6 | 0/6 |
| TE5 | 1→11 | 11 | 2 | 32.0 | 160 | −0.2 | 6/6 | 0/6 |
| Control | 1→11 | 11 | — | 20.0 | — | +0.5 | 10/10 | 0/10 |

Tumor inoculum: 1 × 10⁶ cells from minced tumor brei implanted i.p.
Host: BDF$_1$ ♂ mice.
Me CCNU = methyl CCNU.
CTX = cyclophosphamide.

TABLE 3

Effect of TE-5 and TE-6 on Lewis Lung Carcinoma

| Compound | Dose mg/kg/day | MST Days | Effect MST %T/C | Average Weight Change in g. | Survivors Day 5 | Survivors Day 60 |
|---|---|---|---|---|---|---|
| TE-5 | 2 | 29.5 | 155 | −0.8 | 6/6 | 0/6 |
| TE-5 | 1 | 21.0 | 111 | −0.3 | 6/6 | 0/6 |
| TE-5 | 0.5 | 20.0 | 105 | +0.1 | 6/6 | 0/6 |
| TE-6 | 8 | >60.0 | >325 | −0.8 | 6/6 | 5/6 |
| TE-6 | 4 | >60.0 | >325 | −0.8 | 6/6 | 4/6 |
| TE-6 | 2 | 25.5 | 135 | −0.2 | 6/6 | 1/6 |
| TE-6 | 1 | 22.0 | 115 | −0.9 | 6/6 | 0/6 |
| TE-6 | 0.5 | 21.5 | 113 | −0.1 | 6/6 | 0/6 |
| Control | Saline | 19.0 | — | +1.0 | 10/10 | 0/10 |

Tumor inoculum: 1 × 10⁶ cells from minced tumor brei implanted i.p.
Host: BDF$_1$ ♂ mice.
Treatment: Once daily for 11 days starting Day 1.
TE-6 = compound of Example 2.

TABLE 4

Effect of Chloroethylnitrosourea Compounds on L-1210 Leukemia

| Compound | Dose mg/kg/day | MST Days | Effect MST %T/C | Average Weight Change in g. | Survivors Day 5 | Survivors Day 30 |
|---|---|---|---|---|---|---|
| TE-5 | 32 | >30.0 | >428 | −1.1 | 6/6 | 3/6 |
| TE-5 | 16 | 9.5 | 136 | −0.3 | 6/6 | 0/6 |
| TE-5 | 8 | 7.0 | 100 | +0.6 | 6/6 | 0/6 |
| TE-5 | 4 | 6.5 | 93 | +1.3 | 6/6 | 0/6 |
| TE-5 | 2 | 7.0 | 100 | +2.0 | 6/6 | 0/6 |
| TE-5 | 1 | 7.0 | 100 | +1.3 | 6/6 | 0/6 |
| TE-5 | 0.5 | 7.0 | 100 | −1.1 | 6/6 | 0/6 |
| TE-6 | 32 | >30.0 | >428 | −1.3 | 6/6 | 3/6 |
| TE-6 | 16 | >30.0 | >428 | −1.6 | 6/6 | 3/6 |
| TE-6 | 8 | 13.0 | 186 | −0.8 | 6/6 | 0/6 |
| TE-6 | 4 | 10.5 | 150 | −2.6 | 6/6 | 0/6 |
| TE-6 | 2 | 9.0 | 136 | −2.0 | 6/6 | 0/6 |
| TE-6 | 1 | 7.0 | 100 | +1.3 | 6/6 | 0/6 |
| TE-6 | 0.5 | 7.0 | 100 | −0.5 | 6/6 | 0/6 |
| CCNU (NSC79037) | 32 | 14.0 | 200 | −2.5 | 6/6 | 0/6 |
| | 16 | 16.5 | 236 | −1.3 | 6/6 | 0/6 |

TABLE 4-continued
Effect of Chloroethylnitrosourea Compounds on L-1210 Leukemia

| Compound | Dose mg/kg/day | MST Days | Effect MST %T/C | Average Weight Change in g. | Survivors Day 5 | Day 30 |
|---|---|---|---|---|---|---|
|  | 8 | 12.5 | 179 | −0.6 | 6/6 | 0/6 |
|  | 4 | 8.5 | 121 | −0.3 | 6/6 | 0/6 |
|  | 2 | 7.0 | 100 | +0.6 | 6/6 | 0/6 |
|  | 1 | 7.0 | 100 | +1.7 | 6/6 | 0/6 |
|  | 0.5 | 6.5 | 93 | +0.8 | 6/6 | 0/6 |
| BCNU | 32 | 8.0 | 114 | −3.3 | 6/6 | 0/6 |
| (NSC409962) | 16 | 15.0 | 214 | −1.3 | 5/5 | 0/5 |
|  | 8 | 18.0 | 257 | −2.1 | 6/6 | 0/6 |
|  | 4 | 12.5 | 179 | −1.5 | 6/6 | 0/6 |
|  | 2 | 8.0 | 114 | 0 | 6/6 | 0/6 |
|  | 1 | 7.0 | 100 | +2.0 | 6/6 | 0/6 |
|  | 0.5 | 7.0 | 100 | +3.3 | 6/6 | 0/6 |
| Control | Saline | 7.0 | — | +0.1 | 10/10 | 0/10 |

Tumor inoculum: 10⁶ ascitic cells implanted i.p.
Host: BDF₁ ♂ mice.
Treatment: Once daily for 9 days starting day 1.

TABLE 5
Effect of Chloroethylnitrosourea Compounds on L-1210 Leukemia

| Compound | Dose mg/kg/day | MST Days | Effect MST %T/C | Average Weight Change in g. | Survivors Day 5 | Day 30 |
|---|---|---|---|---|---|---|
| TE-5 | 32 | 10.0 | 143 | −0.3 | 6/6 | 0/6 |
| TE-5 | 16 | 12.0 | 171 | −0.7 | 6/6 | 0/6 |
| TE-5 | 8 | 23.5 | 336 | +0.9 | 6/6 | 1/6 |
| TE-5 | 4 | 16.0 | 229 | +0.8 | 6/6 | 0/6 |
| TE-5 | 2 | 12.0 | 171 | +1.5 | 6/6 | 0/6 |
| TE-5 | 1 | 8.0 | 114 | +2.3 | 6/6 | 0/6 |
| TE-5 | 0.5 | 7.5 | 107 | +3.1 | 6/6 | 0/6 |
| TE-5 | 0.25 | 7.0 | 100 | +3.8 | 6/6 | 0/6 |
| TE-6 | 32 | 13.0 | 186 | −0.8 | 6/6 | 0/6 |
| TE-6 | 16 | >33.0 | >471 | −0.3 | 6/6 | 6/6 |
| TE-6 | 8 | >33.0 | >471 | +1.0 | 6/6 | 3/6 |
| TE-6 | 4 | 17.5 | 250 | +0.6 | 6/6 | 1/6 |
| TE-6 | 2 | 10.0 | 143 | +2.1 | 6/6 | 0/6 |
| TE-6 | 1 | 8.0 | 114 | +2.3 | 6/6 | 0/6 |
| TE-6 | 0.5 | 8.0 | 114 | +2.3 | 6/6 | 0/6 |
| TE-6 | 0.25 | 7.5 | 107 | +2.5 | 6/6 | 0/6 |
| TE-7 | 32 | 12.0 | 171 | 0 | 5/5 | 0/5 |
| TE-7 | 16 | >33.0 | >471 | −0.3 | 6/6 | 4/6 |
| TE-7 | 8 | 17.0 | 243 | +0.8 | 5/5 | 0/5 |
| TE-7 | 4 | 14.5 | 207 | +1.1 | 6/6 | 1/6 |
| TE-7 | 2 | 15.5 | 221 | +1.1 | 6/6 | 0/6 |
| TE-7 | 1 | 11.0 | 157 | +2.0 | 6/6 | 0/6 |
| TE-7 | 0.5 | 8.0 | 114 | +3.6 | 6/6 | 0/6 |
| TE-7 | 0.25 | 8.0 | 114 | +2.9 | 6/6 | 0/6 |
| BCNU | 32 | 13.5 | 193 | −0.1 | 6/6 | 1/6 |
| (NSC409962) | 16 | >33.0 | >471 | −0.3 | 6/6 | 6/6 |
|  | 8 | 20.5 | 293 | +1.8 | 6/6 | 0/6 |
|  | 4 | 13.5 | 193 | +2.1 | 6/6 | 0/6 |
|  | 2 | 8.0 | 114 | +2.6 | 6/6 | 0/6 |
|  | 1 | 7.0 | 100 | +1.6 | 5/5 | 0/5 |
|  | 0.5 | 7.0 | 100 | +3.8 | 6/6 | 0/6 |
|  | 0.25 | 7.0 | 100 | +3.3 | 6/6 | 0/6 |
| Control, Saline | — | 7.0 | — | +4.2 | 10/10 | 0/10 |

Tumor inoculum: 10⁶ ascitic cells implanted i.p.
Host: BDF₁ ♂ mice.
Treatment: Once daily for 8 days starting day 1.

TABLE 6
Effect of Chloroethylnitrosourea Compounds on Lewis Lung Carcinoma

| Compound | Dose mg/kg/day | MST Days | Effect MST %T/C | Average Weight Change in g. | Survivors Day 5 | Day 60 |
|---|---|---|---|---|---|---|
| TE-6 | 8 | >60.0 | >272 | +0.4 | 5/5 | 4/5 |
| TE-6 | 4 | 41.0 | 186 | +0.2 | 5/5 | 2/5 |
| TE-6 | 2 | >60.0 | >272 | +1.8 | 5/5 | 3/5 |
| TE-6 | 1 | 21.5 | 98 | +1.2 | 6/6 | 1/6 |
| TE-6 | 0.5 | 20.0 | 91 | +21. | 6/6 | 1/6 |
| TE-7 | 16 | 14.0 | 64 | −0.4 | 6/6 | 0/6 |
| TE-7 | 8 | >60.0 | >272 | +1.1 | 6/6 | 6/6 |
| TE-7 | 4 | >60.0 | >272 | +0.1 | 6/6 | 4/6 |
| TE-7 | 2 | >60.0 | >272 | +1.5 | 6/6 | 6/6 |
| TE-7 | 1 | >60.0 | >272 | +0.8 | 5/5 | 4/5 |
| TE-7 | 0.5 | 19.5 | 89 | +1.3 | 6/6 | 0/6 |
| CCNU | 16 | 50.0 | 227 | +0.5 | 5/5 | 1/5 |
| (NSC79037) | 8 | >60.0 | >272 | −1.4 | 6/6 | 3/6 |

TABLE 6-continued

Effect of Chloroethylnitrosourea Compounds on Lewis Lung Carcinoma

| Compound | Dose mg/kg/day | MST Days | Effect MST %T/C | Average Weight Change in g. | Survivors Day 5 | Survivors Day 60 |
|---|---|---|---|---|---|---|
| | 4 | 22.0 | 100 | −2.3 | 6/6 | 0/6 |
| | 2 | 22.0 | 100 | −0.5 | 6/6 | 2/6 |
| | 1 | 20.5 | 93 | −0.8 | 6/6 | 1/6 |
| Control | Saline | 22.0 | — | −1.7 | 10/10 | 0/10 |

Tumor inoculum: $2 \times 10^6$ cells from minced tumor brei implanted i.p.
Host: BDF$_1$ ♂ mice.
Treatment: Once daily for 11 days starting day 1.
Preparation: Fresh daily.
TE-7 = Compound of Example 3.

Summary of Results

Table 1: Compound TE-5 was tested on P-388 lymphatic leukemia and found highly active at 16 mg/kg/day and probably toxic at 32 mg/kg/day.

Table 2: Lewis Lung Carcinoma has been found highly responsive to the clinically active nitrosoureas, CCNU, BCNU and methyl CCNU. All three of these compounds plus cyclophosphamide (CTX) were tested on regimens considered optimal for each in experiments conducted by Mayo, et al, in Cancer Chemotherapy Rep. 56:183–195 (1972). TE-5 was tested on two schedules: (1) 2 doses on days 7 and 14 and (2) daily dosing for 11 days. This particular tumor inoculum was quite resistant since responses were weak and BCNU and CTX were not active at all. TE-5 was active at one dose only on the delayed therapy regimen and somewhat more active by daily dosing. The maximum tolerated dose (MTD) appeared to be 4 mg/kg/day.

Table 3: Compound TE-6 was tested on Lewis Lung Carcinoma along with a retest of TE-5. TE-6 gave striking antitumor effects at 8 and 4 mg/kg/day and resulted in 9/12 long term survivors at these doses.

Table 4: Compounds TE-5 and TE-6 were tested on L-1210 leukemia versus CCNU and BCNU. With respect to TE-5, it was assumed that the dose of 32 mg/kg/day and possibly 16 mg/kg/day was in the toxic range. On the daily dose schedule employed, TE-6 appeared to be superior to TE-5, CCNU and BCNU.

Table 5: TE-5, TE-6 and TE-7 were tested on L-1210 leukemia versus BCNU. The minimum effective dose (MED) was lowest with TE-7 and the optimum dose of 16 mg/kg/day gave comparable results with TE-6, TE-7 and BCNU. TE-5 was slightly less active.

Table 6: TE-6 and TE-7 were compared with CCNU in a test against Lewis Lung Carcinoma. TE-7 seemed superior with 20/83 (87%) of the animals surviving which were treated with doses of 8 through 1 mg/kg/day.

The compounds of the present invention exhibit a wide range of effectiveness against various experimental tumor systems, e.g. P-388 lymphatic leukemia, Lewis Lung Carcinoma and L-1210 leukemia. They may be administered either alone or in combination with other antitumor agents. They are generally administered parenterally in the form of pharmaceutical compositions, i.e. mixtures of the active agents with suitable pharmaceutical carriers or diluents. A suggested human dosage is 6 to 24 mg./M²/day given intravenously for up to 10 days for each course of treatment. These values are illustrative only, however, and the physician will ultimately determine the dosage most suitable for a particular patient on the basis of factors such as age, weight, severity and type of symptoms and the particular agent to be administered.

The following examples are not limiting but are illustrative of this invention. Amberlite IR-120 is a strongly acidic cation exchanger having a styrenedivinylbenzene matrix manufactured by Rohm and Haas, Washington Square, Philadelphia, Pa. Amberlite IRA-400 is a strongly basic anion exchanger having a styrenedivinylbenzene matrix and also manufactured by Rohm and Haas.

EXAMPLE 1

(1,4/2,3,5)-5-[3-(Chloroethyl)-3-nitrosoureido]-1,2,3,4-cyclopentanetetrol (TE-5)

A. (1,4/2,3,5)-5-Amino-1,2,3,4-cyclopentanetetrol (1.0 g.) as prepared in Bull. Chem. Soc. Japan, 44, 2222 (1971) was dissolved in ice cold water (20 ml.) and 2-chloroethyl isocyanate (0.84 ml.) was added to the solution under ice cooling with mechanical agitation. After 2 hours the reaction mixture showed an absence of the starting material on thin layer chromatography in 50% aqueous ethanol as a solvent system. The solution was evaporated under reduced pressure and the residue was dissolved in methanol (3.0 ml.). The methanolic solution was settled in a refrigerator to give 0.56 g. of product. From the mother liquor, the second crop of the product (0.20 g.) was obtained. Recrystallization from ethanol afforded 0.53 g. (31% yield) of (1,4/2,3,5)-5-[3-(2-chloroethyl)ureido]-1,2,3,4-cyclopentanetetrol, m.p. 126°–129° C.

Anal. Calc'd. for $C_8H_{15}N_2O_5Cl$: C, 37.73; H, 5.94; N, 11.00; Cl, 13.92.
Found: C, 37.38; H, 5.85; N, 10.77; Cl, 13.62.

B. The ureido intermediate of part A (329 mg.) was dissolved in 99% formic acid (5.5 ml.) and sodium nitrite (268 mg.) was added to the solution under ice cooling with agitation. After one hour, ice cold water was added to the solution after which the solution was deionized with Amberlite IR-120 (H+) and evaporated under reduced pressure. The residue was dissolved in methanol and evaporated again. This treatment was repeated several times to remove formic acid. The residue was dissolved in absolute ethanol and ether was added to the solution until slightly turbid. The mixture was settled in a refrigerator to give 148 mg. (40% yield) of title product, m.p. 110°–113° C. (decomposition).

Anal. Calc'd. for $C_8H_{14}N_3O_6Cl$: C, 33.87; H, 4.98; N, 14.81; Cl, 12.50.
Found: C, 32.11; H, 4.57; N, 13.85; Cl, 13.19.

EXAMPLE 2

(1,2,3,4/5)-5-[3-(2-Chloroethyl)-3-nitrosoureido]-1,2,3,4-cyclopentanetetrol (TE-6)

A. Tetra-O-acetyl-(1,2,3,4/5)-5-acetamido-1,2,3,4-cyclopentanetetrol (2.14 g.) as prepared in J. Org. Chem., 38, 3691 (1973) was heated in 6N HCl (50 ml.) under reflux for 2 hours and then evaporated under reduced pressure. The residue was dissolved in water and the solution was passed through a column of Amberlite IRA-400 (OH−). The effluent was evaporated under reduced pressure to give 0.90 g. of (1,2,3,4/5)-5-amino-1,2,3,4-cyclopentanetetrol as a pale yellow syrup.

B. The product of part A (0.93 g.) was dissolved in ice cold water (17.5 ml.), and 2-chloroethyl isocyanate (1.05 ml.) was added to the solution under ice cooling with mechanical agitation. After 2 hours, the reaction mixture was filtered and the filtrate was evaporated under reduced pressure. The residue was recrystallized from methanol to give 636 mg. (42% yield) of 1,2,3,4/5)-5-[3-(2-chloroethyl)ureido]-1,2,3,4-cyclopentanetetrol, m.p. 124°–128° C.

C. The compound of part B (575 mg.) was dissolved in 99% formic acid (10 ml.) and sodium nitrite (467 mg.) was added to the solution under ice cooling with agitation. The reaction mixture was worked up as described in Example 1, part B, to give a syrup. The syrup was dissolved in a small volume of ethanol and the solution was settled in a refrigerator to give 290 mg. (45% yield) of title product, m.p. 109° C. (decomposition).

Anal. Calc'd. for $C_8H_{14}N_3O_6Cl$: C, 33.87; H, 4.98; N, 14.81; Cl, 12.50.
Found: C, 34.82; H, 5.08; N, 14.13; Cl, 11.94.

EXAMPLE 3

DL-(1,2,4/3,5)-5-[3-(2-Chloroethyl)-3-nitrosoureido]-1,2,3,4-cyclopentanetetrol (TE-7)

A. DL-(1,2,4/3,5)-5-Amino-1,2,3,4-cyclopentanetetrol (1.81 g.) as prepared in Bull. Chem. Soc. Japan, 46, 2562 (1973) was dissolved in ice cold water (34 ml.) and 2-chloroethyl isocyanate (2.04 ml.) was added to the solution under ice cooling with agitation. After 2 hours, the reaction mixture was filtered and the filtrate was evaporated under reduced pressure to give crystalline residue. Recrystallization from methanol afforded 1.90 g. (62% yield) of DL-(1,2,4/3,5)-5-[3-(2-chloroethyl)ureido]-1,2,3,4-cyclopentanetetrol, m.p. 127°–129° C.

Anal. Calc'd. for $C_8H_{15}N_2O_5Cl$: C, 37.73; H, 5.94; N, 11.00; Cl, 13.92.
Found: C, 37.85; H, 5.84; N, 11.01; Cl, 14.07.

B. The product of part A (776 mg.) was dissolved in 99% formic acid (14 ml.) and sodium nitrite (641 mg.) was added to the solution under ice cooling with agitation. The solution was worked up as described in Example 1, part B, to give a crystalline residue. The residue was digested with ethanol to give 565 mg. (66% yield) of DL-(1,2,4/3,5)-5-[3-(2-chloroethyl-3-nitrosoureido]-1,2,3,4-cyclopentanetetrol, m.p. 129°–131° C. (decomposition).

Anal. Calc'd. for $C_8H_{14}N_3O_6Cl$: C, 33.87; H, 4.98; N, 14.81; Cl, 12.50.
Found: C, 33.64; H, 4.88; N, 15.00; Cl, 12.28.

EXAMPLE 4

If the procedure employed in Example 2 is repeated using in place of the tetra-O-acetyl-(1,2,3,4/5)-5-acetamido-1,2,3,4-cyclopentanetetrol used therein an equimolar amount of the following starting materials:

Tetra-O-acetyl-DL-(1,2,3,5/4)-5-acetamido-1,2,3,4-cyclopentanetetrol
Tetra-O-acetyl-(1,4,5/2,3)-5-acetamido-1,2,3,4-cyclopentanetetrol
Tetra-O-acetyl-DL-(1,3,5/2,4)-5-acetamido-1,2,3,4-cyclopentanetetrol
Tetra-O-acetyl-DL-(1,2,4,5/3)-5-acetamido-1,2,3,4-cyclopentanetetrol
Tetra-O-acetyl-(1,2,3,4,5/0)-5-acetamido-1,2,3,4-cyclopentanetetrol
Tetra-O-acetyl-DL-(1,2,3/4,5)-5-acetamido-1,2,3,4-cyclopentanetetrol
Tetra-O-acetyl-DL-(1,2,5/3,4)-5-acetamido-1,2,3,4-cyclopentanetetrol, there are produced the following products respectively:

DL-(1,2,3,5/4)-5-[3-(2-chloroethyl)-3-nitrosoureido]-1,2,3,4-cyclopentanetetrol
(1,4,5/2,3)-5-[3-(2-chloroethyl)-3-nitrosoureido]-1,2,3,4-cyclopentanetetrol
DL-(1,3,5/2,4)-5-[3-(2-chloroethyl)-3-nitrosoureido]-1,2,3,4-cyclopentanetetrol
DL-(1,2,4,5/3)-5-[3-(2-chloroethyl)-3-nitrosoureido]-1,2,3,4-cyclopentanetetrol
(1,2,3,4,5/0)-5-[3-(2-chloroethyl)-3-nitrosoureido]-1,2,3,4-cyclopentanetetrol
DL-(1,2,3/4,5)-5-[3-(2-chloroethyl)-3-nitrosoureido]-1,2,3,4-cyclopentanetetrol, and
DL-(1,2,5/3,4)-5-[3-(2-chloroethyl)-3-nitrosoureido]-1,2,3,4-cyclopentanetetrol.

The starting materials used above are disclosed in the literature, e.g. J. Org. Chem. 31:4154 (1966), Bull. Chem. Soc. Japan 44:2222-2225 (1971) and J. Org. Chem. 38(21):3691-3696 (1973).

I claim:

1. Antitumor agents having the formula

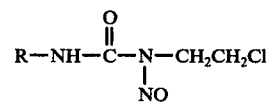

$$R-NH-\overset{O}{\underset{}{C}}-\underset{NO}{N}-CH_2CH_2Cl \qquad I$$

wherein R represents a 2′, 3′, 4′, 5′-tetrahydroxycyclopentyl group.

2. An antitumor agent of claim 1 selected from
(1,4/2,3,5)-5-[3-(2-chloroethyl)-3-nitrosoureido]-1,2,3,4-cyclopentanetetrol,
(1,2,3,4/5)-5-[3-(2-chloroethyl)-3-nitrosoureido]-1,2,3,4-cyclopentanetetrol and
DL-(1,2,4/3,5)-5-[3-(2-chloroethyl)-3-nitrosoureido]-1,2,3,4-cyclopentanetetrol.

3. The compound of claim 1 named (1,4/2,3,5)-5-[3-(2-chloroethyl)-3-nitrosoureido]-1,2,3,4-cyclopentanetetrol.

4. The compound of claim 1 named (1,2,3,4/5)-5-[3-(2-chloroethyl)-3-nitrosoureido]-1,2,3,4-cyclopentanetetrol.

5. The compound of claim 1 named DL-(1,2,4/3,5)-5-[3-(2-chloroethyl)-3-nitrosoureido]-1,2,3,4-cyclopentanetetrol.

6. The compound of claim 1 named DL-(1,2,3,5/4)-5-[3-(2-chloroethyl)-3-nitrosoureido]-1,2,3,4-cyclopentanetetrol.

7. The compound of claim 1 named (1,4,5/2,3)-5-[3-(2-chloroethyl)-3-nitrosoureido]-1,2,3,4-cyclopentanetetrol.

8. The compound of claim 1 named DL-(1,3,5/2,4)-5-[3-(2-chloroethyl)-3-nitrosoureido]-1,2,3,4-cyclopentanetetrol.

9. The compound of claim 1 named DL-(1,2,4,5/3)-5-[3-(2-chloroethyl)-3-nitrosoureido]-1,2,3,4-cyclopentanetetrol.

10. The compound of claim 1 named (1,2,3,4,5/0)-5-[3-(2-chloroethyl)-3-nitrosoureido]-1,2,3,4-cyclopentanetetrol.

11. The compound of claim 1 named DL-(1,2,3/4,5)-5-[3-(2-chloroethyl)-3-nitrosoureido]-1,2,3,4-cyclopentanetetrol.

12. The compound of claim 1 named DL-(1,2,5/3,4)-5-[3-(2-chloroethyl-3-nitrosoureido]-1,2,3,4-cyclopentanetetrol.

* * * * *